United States Patent
Rivier

(10) Patent No.: US 10,048,279 B2
(45) Date of Patent: Aug. 14, 2018

(54) METHOD FOR THE DIAGNOSIS OF ROSACEA

(71) Applicant: GALDERMA RESEARCH & DEVELOPMENT, Biot (FR)

(72) Inventor: Michel Rivier, Nice (FR)

(73) Assignee: GALDERMA RESEARCH & DEVELOPMENT, Biot (FR)

( * ) Notice: Subject to any disclaimer, the term of this patent is extended or adjusted under 35 U.S.C. 154(b) by 0 days.

(21) Appl. No.: 14/365,936

(22) PCT Filed: Dec. 14, 2012

(86) PCT No.: PCT/EP2012/075482
§ 371 (c)(1),
(2) Date: Jun. 16, 2014

(87) PCT Pub. No.: WO2013/087809
PCT Pub. Date: Jun. 20, 2013

(65) Prior Publication Data
US 2014/0349882 A1 Nov. 27, 2014

Related U.S. Application Data

(60) Provisional application No. 61/576,712, filed on Dec. 16, 2011.

(51) Int. Cl.
*C12Q 1/68* (2018.01)
*G01N 33/74* (2006.01)
*C12Q 1/6883* (2018.01)

(52) U.S. Cl.
CPC .......... *G01N 33/74* (2013.01); *C12Q 1/6883* (2013.01); *C12Q 2600/112* (2013.01); *C12Q 2600/118* (2013.01); *C12Q 2600/158* (2013.01); *G01N 2800/202* (2013.01); *G01N 2800/24* (2013.01); *G01N 2800/328* (2013.01)

(58) Field of Classification Search
CPC .. G01N 33/74; G01N 800/202; G01N 800/24; G01N 800/328; C12Q 1/6883; C12Q 600/112; C12Q 600/118; C12Q 600/158
See application file for complete search history.

(56) References Cited

FOREIGN PATENT DOCUMENTS

| WO | 2010/007175 A2 | 1/2010 |
|---|---|---|
| WO | 2011/073321 A1 | 6/2011 |

OTHER PUBLICATIONS

Zamlynski et al., Galanin concentrations in maternal circulation, amniotic fluid and umbilical cord blood during term labor: relationship with maternal body mass and neonatal birth weight, Gynecol Endocrinol. May 2007;23(5):295-9.*

International Search Report and Written Opinion dated Mar. 27, 2013 corresponding to International Patent Application No. PCT/EP2012/075482, 15 pages.

(Continued)

*Primary Examiner* — Reza Ghafoorian
(74) *Attorney, Agent, or Firm* — Dentons US LLP

(57) ABSTRACT

A method is described for the diagnosis of rosacea. The method can include a step of measuring the expression of at least one peptide from the galanin family in a sample of biological fluid from a patient. Also described, is a related diagnostic kit.

12 Claims, 2 Drawing Sheets

| Affymetrix identifier | Gene Name | Gene Symbol | PSORIASIS GSE1355 Relative Induction Psoriasis patients versus healthy controls | PSORIASIS GSE14905 Relative Induction Psoriasis patients versus healthy | ROSACEA TYPE I Relative Induction Rosacea patients versus | ROSACEA TYPE II Relative Induction Rosacea patients versus | ROSACEA TYPE III Relative Induction Rosacea patients versus | ACNE Relative Induction Lesional skin versus healthy | ATOPIC DERMATITIS Relative Induction Atopic patients versus healthy controls |
|---|---|---|---|---|---|---|---|---|---|
| 214240_at | galanin preopropeptid | GAL | -6.27 | -6.63 | 14.2 | 3.41 | 6.95 | -3.31 | -1.41 |
| 220821_at | galanin receptor 1 | GALR1 | ND | ND | ND | ND | ND | ND | ND |
| 211226_at | galanin receptor 2 | GALR2 | ND | ND | 1.07 | 1.16 | 1.2 | ND | ND |
| 33579_i_at | galanin receptor 3 | GALR3 | ND | 1.12 | 1.24 | 1.07 | 1.03 | 1.08 | -1.04 |

(56) References Cited

OTHER PUBLICATIONS

Schwab, V. D., et. al., "Neurovascular and Neuroimmune Aspects in the Pathophysiology of Rosacea," Journal of Investigative Dermatology Symposium Proceedings, vol. 15, No. 1, Dec. 2011, pp. 53-62.

Kim, K. Y., et al., "Galanin Is Up-Regulated in Colon Adenocarcinoma," Cancer Epidemiology, Biomarkers & Prevention, vol. 16, No. 11, Nov. 2007, pp. 2373-2378.

Greenbaum, Dov, et al., "Comparing protein abundance and mRNA expression levels on a genomic scale," Genome Biology (Online), Biomed Central Ltd, GB, vol. 40, No. 9, Jan. 2003, pp. 117.01-117.8.

Greenbaum, Dov, et al., "Interrelating Different Types of Genomic Data, from Proteome to Secretome: Oming in on Function," Genome Research, Cold Spring Harbor Lab. Press, Woodbury, NY, vol. 11, No. 9, Sep. 2001, pp. 1463-1468.

Oerntoft, T. F., et al., "Genome-wide Study of Gene Copy Numbers, Transcripts, and Protein Levels in Pairs of Non-invasive and Invasive Human Transitional Cell Carcinomas," Molecular & Cellular Proteomics, Am. Soc. for Biochemistry and Molecular Biology, Inc., vol. 1, No. 1, Jan. 2002, pp. 37-45.

\* cited by examiner

FIG. 1

| Affymetrix Identifier | Gene Name | Gene Symbol | PSORIASIS GSE1355 Relative Induction Psoriasis patients versus healthy controls | PSORIASIS GSE14905 Relative Induction Psoriasis patients versus healthy | ROSACEA TYPE I Relative Induction Rosacea patients versus | ROSACEA TYPE II Relative Induction Rosacea patients versus | ROSACEA TYPE III Relative Induction Rosacea patients versus | ACNE Relative Induction Lesional skin versus healthy | ATOPIC DERMATITIS Relative Induction Atopic patients versus healthy controls |
|---|---|---|---|---|---|---|---|---|---|
| 214240_at | galanin prepropeptid | GAL | -6.27 | -6.63 | 14.2 | 3.41 | 6.95 | -3.31 | -1.41 |
| 220821_at | galanin receptor 1 | GALR1 | ND | ND | ND | ND | ND | ND | ND |
| 211226_at | galanin receptor 2 | GALR2 | ND | ND | 1.07 | 1.16 | 1.2 | ND | ND |
| 33579_i_at | galanin receptor 3 | GALR3 | ND | 1.12 | 1.24 | 1.07 | 1.03 | 1.08 | -1.04 |

METHOD FOR THE DIAGNOSIS OF ROSACEA

CROSS-REFERENCE TO PRIOR APPLICATIONS

This application is a National Stage of PCT/EP2012/075482, filed Dec. 14, 2012, and designating the United States (published in English on Jun. 20, 2013, as WO 2013/087809 A1), which claims priority under 35 U.S.C. § 119 to US Provisional Patent Application No. 61/576,712, filed Dec. 16, 2011, each hereby expressly incorporated by reference in its entirety and each assigned to the assignee hereof.

The present invention relates to a method for the diagnosis of rosacea, comprising measuring the expression of a peptide from the galanin family, and more preferably galanin, GMAP, GALP, preproGALP and alarin.

Rosacea is a common, chronic and progressive inflammatory dermatosis related to vascular disorders. It mainly affects the central part of the face and is characterized by blushing and flushing, facial erythema, papules, pustules, telangiectasia and sometimes ocular lesions known as ocular rosacea. In severe cases, particularly in men, rhinophyma, or a bulbous enlargement of the nose, may occur. Rosacea develops over the course of several years with periods of exacerbation triggered by various stimuli such as temperature changes, alcohol, spicy foods, sun exposure and emotional factors.

Rosacea is classified into four subtypes according to clinical features (Wilkin J et al., JAAD, 2002, 46: 584-587).

The primary features of rosacea (vasomotor flushing, persistent erythema, papules and pustules, telangiectasias) often occur in association with secondary symptoms (burning or stinging sensation, plaques, dry skin, edema, eye symptoms, phymatous changes). The visible manifestations or most common combinations of signs are provisionally classified into specific subtypes which are described below:

Subtype 1: Erythematotelangiectatic Rosacea

Erythematotelangiectactic rosacea is mainly characterized by vasomotor flushing and persistent central facial erythema. Telangiectasias are commonly observed but are not essential for the diagnosis of this subtype. Central facial edema, burning or stinging sensations and rough, flaky skin are also symptoms that have sometimes been reported. A history of flushing as the only symptom is commonly found in people with erythematotelangiectatic rosacea.

Subtype 2: Papulopustular Rosacea

Papulopustular rosacea is characterized by persistent central facial erythema and transient crops of papules and/or pustules in the center of the face. However, the papules and pustules can also occur in periorificial regions, i.e., around the mouth, nose and eyes. The papulopustular subtype resembles acne vulgaris, but comedones are absent. Rosacea and acne may coexist in a same patient, in which case comedones may also be present alongside the papules and pustules suggestive of rosacea. People with papulopustular rosacea sometimes complain of a burning or stinging sensation.

This subtype is often observed before or at the same time as subtype 1 (including the presence of telangiectasias). The telangiectasias may be obscured by the persistent erythema and the papules and pustules, but they tend to become more visible after successful treatments that cover up these features.

Subtype 3: Phymatous Rosacea

Phymatous rosacea is characterized by a thickening of the skin, irregular surface nodularities and swelling. The nose is most commonly affected but phymatous rosacea can also involve other areas such as the chin, the forehead, the cheeks and the ears. Patients with this subtype sometimes exhibit prominent, enlarged follicles in the affected areas as well as telangiectasias.

This subtype often occurs before or at the same time as subtypes 1 or 2 (including the presence of persistent erythema, telangiectasias, papules and pustules). In the case of rhinophyma, these additional stigmata may be particularly pronounced in the nasal region.

Subtype 4: Ocular Rosacea (or Ophthalmic Rosacea)

Ocular rosacea is often incorrectly diagnosed or underestimated as a cause of conjunctival inflammation. The diagnosis of ocular rosacea should be considered when a patient presents with one or more of the following ocular signs and symptoms: watery or bloodshot eyes (interpalpebral conjunctival hyperemia), foreign body sensation, burning or stinging, dry or itchy eyes, sensitivity to light, blurred vision, conjunctival telangiectasias or eyelid margin telangiectasias or erythema of the eyelid and periocular area. Blepharitis, conjunctivitis and irregularities of the eyelid margins are other possible signs. A cyst or a chronic staphylococcal infection presenting as a sty, the cause of which is meibomian gland dysfunction, is a common sign of an ocular pathology related to rosacea. Some patients complain of a loss of visual acuity, which is due to corneal complications (punctate keratitis, corneal infiltrates/ulcerations or marginal keratitis). Treatment of only the cutaneous manifestations of rosacea may have no effect on the risk of a loss of vision associated with ocular rosacea, and ophthalmic management will possibly be required.

Ocular rosacea is most often diagnosed when cutaneous signs and symptoms are also present. However, cutaneous manifestations are not necessary for the diagnosis, and studies in small series suggest that up to 20% of patients with the ocular subtype develop ocular manifestations before the emergence of cutaneous findings. In a minority of people, the two subtypes have a simultaneous onset.

Rosacea may therefore progress through several stages although it is not necessary for a patient to experience all stages.

Finally, other, rarer variants of rosacea exist, in particular granulomatous rosacea.

Rosacea has a peak age of onset between 25 and 70 and is much more common in people with a light complexion. It more particularly affects women although the condition is generally more severe in men.

Conventionally, rosacea is treated by the oral or topical route. The conventional topical treatment of rosacea comprises topical application of metronidazole, azelaic acid and/or sodium sulfacetamide-sulfur. Oral treatment comprises doxycycline monohydrate (Nally J B & Berson D S, J Drug Dermatol, 2006, 5: 23-26; Baldwin H E, J Drug Dermatol, 2006, 5: 16-21; Baldwin H E, Skin Therapy Letter, 2007, 12: 1-9). However, existing therapies are not curative and only serve to attenuate the symptoms.

Today, the early diagnosis of rosacea is difficult because it is based mainly on clinical findings (inspection of the skin).

More particularly, the diagnosis of ocular rosacea is complicated by the fact that the clinical picture is often mixed, with both cutaneous and ocular involvement, although ocular symptoms may be the only presenting feature, as noted earlier. In the latter case, it is difficult for the clinician to distinguish between a true ocular rosacea which will subsequently develop cutaneous manifestations, and a simple case of blepharitis or conjunctivitis. As results, the first-line treatments of ocular rosacea presenting with only eye symptoms are often inappropriate and ineffective.

Thus, there is a need to have a method for diagnosing rosacea, and even more ocular rosacea, which is simple, rapid and reliable, and which can be implemented as soon as the first symptoms develop so as to confirm or rule out this pathology.

In particular, the present invention provides a method for the diagnosis of rosacea and more particularly ocular rosacea, which is simple to carry out and at the same time reliable and safe.

The inventors have now discovered that, in a surprising manner, peptides from the galanin family ("galanin peptide family"), present in the tear fluid of patients, are excellent markers of rosacea. The term "marker" as employed herein is intended to mean any biological entity (protein, peptide, messenger RNA or other) which, by measuring the expression thereof, allows the characterization of a difference between two conditions, one healthy and the other pathological, in the presence or not of a treatment.

The present invention therefore has as object a method for the diagnosis of rosacea, comprising a step of measuring the expression of at least one peptide from the galanin family in a sample of biological fluid from the patient. The present invention also relates to a method for providing data useful for the diagnosis of rosacea and more particularly ocular rosacea.

"Peptide from the galanin family" is intended to mean any peptide encoded by the GAL gene or by the preproGALP gene, and as non-limiting examples, galanin, GMAP peptide (Galanin message-associated peptide) or preprogalanin, GALP peptide (Galanin like peptide), its precursor preproGALP, and alarin. In a preferred embodiment, peptide from the galanin family is galanin. In another preferred embodiment, peptide from the galanin family is GMAP.

Galanin is a peptide containing 30 amino acids in humans, encoded by the GAL gene; the human sequence is available in UniProt under the identifier P22466. Galanin plays a role in the control of food intake, cognition, the control of endocrine function and in nociception. In humans, galanin is secreted in the form of a prepropeptide of 123 amino acids. This prepropeptide, called preprogalanin, is cleaved to a propeptide; said propeptide is then cleaved in turn to galanin and an associated peptide (galanin message-associated peptide or GMAP). GMAP is a peptide of 59 or 60 amino acids (Hökfelt T, Tatemoto K (June 2008). "Galanin—25 years with a multitalented neuropeptide". Cell. Mol. Life Sci. 65 (12): 1793-5).

The preproGALP gene encodes different peptides: respectively, GALP containing 60 amino acids, its precursor, a propeptide of 115-120 amino acids depending on the species (116 amino acids in humans, UniProt identifier Q9UBC7) known as PreproGALP, and alarin (49 amino acids in humans, UniProt identifier Q9UBC7-2), which are formed by different post-translational splicings of this preproGALP gene (Lang R, Gundlach A L, Kofler B (August 2007). "The galanin peptide family: receptor pharmacology, pleiotropic biological actions, and implications in health and disease". Pharmacol. Ther. 115 (2): 177-207).

According to one embodiment of the invention, the present invention therefore has as object a method for the diagnosis of rosacea, comprising a step of measuring the expression of galanin in a sample of biological fluid from the patient.

According to another embodiment of the invention, the present invention therefore has as object a method for the diagnosis of rosacea, comprising a step of measuring the expression of GMAP in a sample of biological fluid from the patient.

According to a further embodiment of the invention, the present invention therefore has as object a method for the diagnosis of rosacea, comprising a step of measuring the expression of GALP in a sample of biological fluid from the patient.

According to an additional embodiment of the invention, the present invention therefore has as object a method for the diagnosis of rosacea, comprising a step of measuring the expression of preproGALP in a sample of biological fluid from the patient.

According to another embodiment of the invention, the present invention therefore has as object a method for the diagnosis of rosacea, comprising a step of measuring the expression of alarin in a sample of biological fluid from the patient.

Throughout the present invention, unless otherwise indicated, "peptide from the galanin family" will be employed interchangeably to mean at least one of the following peptides: galanin, GMAP, GALP, preproGALP and alarin. In a preferred embodiment, peptide from the galanin family is galanin. In a preferred embodiment, peptide from galanin family is GMAP.

The diagnostic method according to the invention comprises a step of measuring the expression of at least one peptide from the galanin family in a sample of biological fluid from the patient. The biological fluid is selected in particular from the group consisting of tears, blood, urine and saliva. Preferably, the biological fluid is tears.

"Measuring the expression of a peptide from the galanin family" is intended to mean measuring the amount or the concentration of mRNA coding for galanin and/or another peptide from the galanin family or measuring the amount or concentration of galanin and/or another peptide from the galanin family. Measuring the expression of a peptide from the galanin family according to the invention may be performed by any method known for measuring the quantity of mRNA encoding galanin and/or another peptide from the galanin family, such as quantitative RT-PCR technique or chip techniques. Measuring the expression of a peptide from the galanin family according to the invention is preferably carried out by measuring the amount of a peptide from the galanin family with the aid of an antibody specifically directed at an epitope of said peptide. The reference method used for the detection and quantitative measurement of galanin is an ELISA kit (Enzyme-Linked Immunosorbent Assay, an analytical assay on a solid support allowing the detection of a substance in liquid medium). However, any other analytical quantification method may be used. This comprises in particular methods of quantitative chromatography and detection which are coupled, but also methods for analyzing proteins or peptides after migration through cross-linked gels (type Western Blot). Antibodies directed against peptides from the galanin family are commercially available.

The diagnostic method according to the invention allows the diagnosis of erythematotelangiectatic rosacea, papulopustular rosacea, phymatous rosacea, ocular rosacea. Preferably, it allows the diagnosis of ocular rosacea.

According to the invention, the diagnostic method therefore preferably comprises measuring the amount of at least one peptide from the galanin family or of mRNA encoding therefor, in a biological fluid from the patient, preferably tears. Such method is reliable, rapid and noninvasive.

Preferably, the diagnostic method according to the invention comprises, subsequent to the step of measuring the expression of at least one peptide from the galanin family in a sample of biological fluid from the patient, a step of comparing said at least one peptide from the galanin family expression with a control.

The control may be a sample of the same biological fluid from a healthy patient. The control may also be a solution comprising a known concentration of said at least one peptide from the galanin family. In an embodiment, said peptide is galanin. In a preferred embodiment, the peptide from the galanin family is GMAP.

The step of comparing the expression of at least one peptide from the galanin family in a patient with a control allows a conclusion to be drawn as to a possible overexpression of said peptide.

Thus, overexpression of at least one peptide from the galanin family compared to an unaffected control from a healthy patient is indicative of rosacea. Preferably, a strong overexpression of at least one peptide from the galanin family relative to an unaffected control from a healthy subject is indicative of very severe rosacea. Strong expression is intended to mean an expression of the peptide in the sample from the rosacea patient that is at least 5 times greater than that in the sample from the healthy subject. Said expression may possibly be much greater than a factor of 5. Preferably, moderate overexpression of at least one peptide from the galanin family relative to a control is indicative of moderate rosacea. Moderate is intended to mean an expression of the peptide in the sample from the rosacea patient that is between 2 and 5 times greater than that in the sample from the healthy subject.

These different criteria of severity may be applied to all the subtypes of rosacea and more particularly to ocular rosacea.

The present invention also relates to a rosacea diagnostic kit, comprising the means for detecting and quantifying at least one peptide from the galanin family. Means for detecting may be specific antibodies of at least one peptide from the peptide family, or mRNA specific primers and/or probes encoding a peptide from the galanin family.

The present invention relates to a kit for use as defined above for rosacea diagnostic, in particular, ocular rosacea, or to monitor the response to a rosacea treatment.

The present invention further relates to a method for monitoring the response to a treatment of rosacea, comprising a step of measuring the expression of at least one peptide from the galanin family in a sample of biological fluid from the patient. In a preferred embodiment, said peptide is galanin. In a preferred embodiment, the peptide from the galanin family is GMAP.

As noted earlier, the biological fluid from the patient is selected in particular from the group consisting of tear fluid, blood, urine and saliva.

Said monitoring method according to the invention preferably comprises measuring the amount of mRNA coding for at least one peptide from the galanin family or the amount of at least one peptide from the galanin family. Preferably, it comprises, subsequent to the step of measuring the expression of at least one peptide from the galanin family in a sample of biological fluid from the patient, a step of comparing said expression of the peptide from the galanin family with a control. In this case, the control may be a healthy patient. The control may also be a patient who is a responder or nonresponder to said treatment. Alternatively, the control may be a sample from the same patient but at a different time, for instance before the beginning of the treatment.

The rosacea treatment that can be used in the monitoring method may be any active agent effective in eliminating the symptoms of rosacea, and in particular, ivermectin, metronidazole, clindamycin, azelaic acid, ketoconazole, permethrin, sodium sulfacetamide-sulfur, tretinoin, erythromycin, tetracycline, minocycline, isotretinoin, doxycycline, doxycycline monohydrate or else fusidic acid.

The monitoring method according to the invention thereby allows an evaluation of the efficacy of a given treatment of rosacea, with the aid of a marker which is a peptide from the galanin family, preferably galanin.

The examples that follow are given for purposes of illustration and not by way of limitation.

EXAMPLES

Materials and Methods
Selection of Patients with Different Dermatological Conditions (Rosacea, Acne, Psoriasis, Atopic Dermatitis) and Biopsies
Rosacea:

Skin biopsies from patients suffering from rosacea of subtype I (erythematotelangiectatic; n=11), II (papulopustular; n=11) and III (rhinophyma; n=6) were carried out in accordance with good clinical practice. The clinical description of the patients suffering from rosacea was carried out according to the classification of Wilkin et al., 2002, J. Am. Acad. Dermatol. Vol 46, pages 584-587.

To evaluate a change in the level of messenger RNA (mRNA) expression, the level of expression in affected skin was compared with the level of expression in skin from healthy subjects (n=12).
Acne:

Skin biopsies from patients with acne were obtained from an inflammatory papule and from an unaffected area in 12 patients in accordance with good clinical practice.

To evaluate a change in the level of messenger RNA (mRNA) expression, the level of expression in affected skin was compared with the level of expression in skin from healthy subjects (n=12).
Extraction of Messenger RNA, Labeling and Hybridization on Chips (Acne and Rosacea Patients):

mRNA was isolated from skin samples using the "RNeasy Extraction" kit (Quigen Inc., Valencia, Calif.) and quality was evaluated using the Agilent "2100 Bioanalyzer". mRNA expression was evaluated with the "Gene Chip IVT" labeling kit after synthesizing double stranded complementary DNA (i.e., the process of in vitro transcription) using the "T7-oligo primer" and "One cycle cDNA synthesis" kit from Affymetrix. The RNA was precipitated with ethanol to concentrate the sample and quantified by spectrophotometry. Approximately 200 ng of total RNA of good quality [RNA indication number (RIN)≥7] from each sample were used to synthesize the double stranded cDNA using the T7-oligo primer (dt) (one cycle cDNA synthesis kit, Affymetrix). Biotinylated cRNA produced through in vitro transcription (Gene Chip IVT labeling kit, Affymetrix) was fragmented and hybridized on Affymetrix human U133A 2.0 plus arrays. Arrays were treated with the "Gene Chip Fluidics Station 450" and scanned on the Affymetrix Gene Chip scanner (Santa Clara, Calif.).
Psoriasis and Atopic Dermatitis:

Gene expression data from skin biopsies of patients suffering from psoriasis and atopic dermatitis were extracted from the Gene Expression Omnibus database (National Center for Biotechnology Information).

Expression data from the skin of 10 patients with atopic dermatitis came from study GSE6012 (Olsson M, Broberg A, Jernås M, Carlsson L, Rudemo M, Suurküla M, Svensson P A, Benson M. Increased expression of aquaporin 3 in atopic eczema. Allergy. 2006 September; 61(9):1132-7). Ten patients with healthy skin were used as controls.

Expression data for psoriasis came from a study of 58 patients with psoriasis and 64 healthy subjects (GSE13355; Nair R P, Duffin K C, Helms C, Ding J, Stuart P E, Goldgar D, Gudjonsson J E, Li Y, Tejasvi T, Feng B J, Ruether A, Schreiber S, Weichenthal M, Gladman D, Rahman P, Schrodi S J, Prahalad S, Guthery S L, Fischer J, Liao W, Kwok P Y, Menter A, Lathrop G M, Wise C A, Begovich A B, Voorhees J J, Elder J T, Krueger G G, Bowcock A M, Abecasis G R; Collaborative Association Study of Psoriasis. Genome-wide scan reveals association of psoriasis with IL-23 and NF-kappaB pathways. Nat Genet. 2009 February; 41(2):199-204) and from a study of 28 patients with psoriasis and 21 healthy subjects (GSE14905; Yao Y, Richman L, Morehouse C, de los Reyes M et al. Type I interferon: potential therapeutic target for psoriasis? PLoS One 2008 Jul. 16; 3(7):e2737).

Statistical Analysis:

Expression data were normalized by the RMA method (Robust Multi-array Analysis). Intensity values were corrected for background noise, transformed to base 2 logarithm and normalized by quantile. A linear model was used to normalize the data in order to obtain expression levels for each probe in each array. To identify genes that were significantly modulated in the different samples, a one-way ANOVA with Benjamini-Hochberg multiplicity correction was carried out using MP7.01 (SAS Institute) and irMF 3.5 (National Institute of Statistical Sciences, NISS).

FIG. 1 represents a table of the mRNA expression data in different pathologies (rosacea, acne, psoriasis, atopic dermatitis). In the table, "ND" means not detected.

FIGS. 1 and 2 show GAL gene expression and transcription in mRNA in different pathologies (rosacea, acne, psoriasis, atopic dermatitis).

Figure 2:
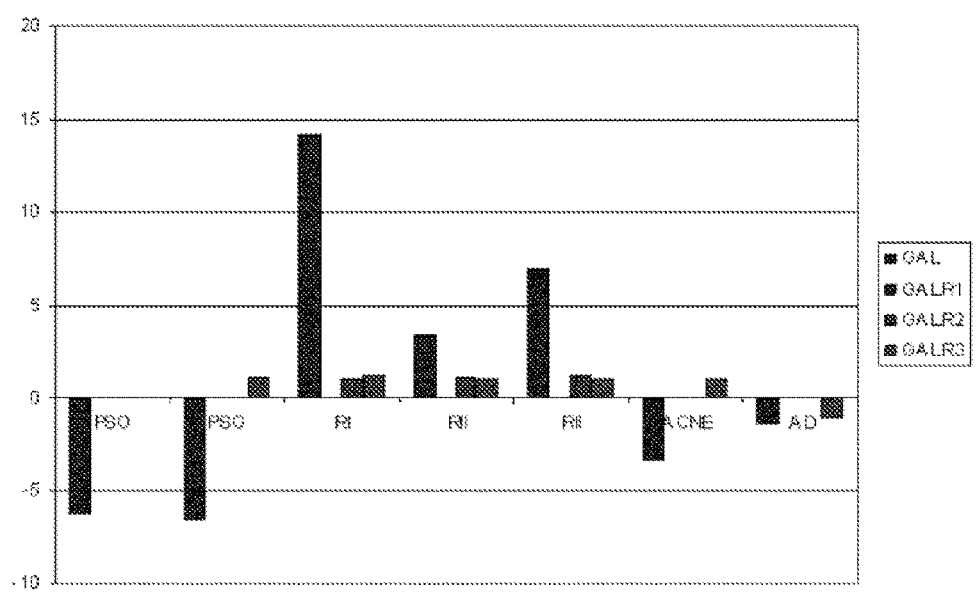
FIG. 2 represents a bar graph of the mRNA expression data from Table 1.

These results show that mRNA of GAL gene from skin were strongly expressed in the skin in patients with rosacea and not expressed in the skin of patients with psoriasis, acne or atopic dermatitis. These results also show that the expression of the three galanin receptors—GALR1, GALR2 and GALR3—did not vary.

These findings clearly demonstrate that these markers are specific of rosacea.

The invention claimed is:

1. A method for diagnosing and treating rosacea, the method comprising:
    measuring an expression level of at least one peptide from the galanin family in a sample of biological fluid from a patient, wherein the biological fluid sample is selected from the group consisting of at least one tear, urine, and saliva;
    comparing the measured expression level of the at least one peptide to a control sample comprising a known healthy concentration of at least one peptide from the galanin family; and
    diagnosing the patient with rosacea when the expression level of the at least one peptide in the biological fluid from the patient is at least 5 times greater than the known healthy concentration of the control sample; and
    when the patient is diagnosed with rosacea, administering to the patient an effective amount of ivermectin, metronidazole, clindamycin, azelaic acid, ketoconazole, permethrin, sodium sulfacetamide-sulfur, tretinoin, erythromycin, tetracycline, minocycline, isotretinoin, doxycycline, doxycycline monohydrate, or fusidic acid;
wherein the effective amount is effective in eliminating at least one symptom of rosacea.

2. A method for the diagnosis of rosacea, the method comprising:
    measuring the expression of at least one peptide from the galanin family in a sample of biological fluid from a patient;
    comparing the measured expression level of the at least one peptide to a control sample comparison a known healthy concentration of at least one peptide from the galanin family; and
    diagnosing the patient with rosacea when the expression level of the at least one peptide from the biological fluid from the patient is at least 5 times greater than the known healthy concentration of the control sample;
    wherein the biological fluid sample is selected from the group consisting of tears, urine, and saliva; and
    wherein the rosacea is selected from the group consisting of erythematotelangiectatic rosacea, papulopustular rosacea, and ocular rosacea.

3. A method for monitoring a response to a treatment of rosacea, the method comprising:
    measuring the expression of at least one peptide from the galanin family in a sample of biological fluid from a patient, wherein the biological fluid sample is selected from the group consisting of tears, urine, and saliva;
    comparing the measured expression level of the at least one peptide to a control sample comprising a known healthy concentration of at least one peptide from the galanin family; and
    when then the level of the biological fluid from the patient is at least 5 times greater than the known healthy concentration of the control sample, administering to the patient an effective amount of ivermectin, metronidazole, clindamycin, azelaic acid, ketoconazole, permethrin, sodium sulfacetamide-sulfur, tretinoin, erythromycin, tetracycline, minocycline, isotretinoin, doxycycline, doxycycline monohydrate, or fusidic acid, wherein the effective amount is effective in eliminating at least one symptom of rosacea.

4. The method according to claim 2, wherein the step of measuring the expression of the at least one peptide from the galanin family comprises measuring an amount of mRNA coding for peptide(s) from the galanin family.

5. A method for monitoring a response to a treatment of rosacea and treating rosacea, the method comprising:
    measuring the expression of at least one peptide from the galanin family in a sample of biological fluid from a patient diagnosed with rosacea, wherein the biological fluid sample is selected from the group consisting of at least one tear, urine, and saliva;
    comparing the measured expression level to a control sample comprising a known healthy concentration of the at least one peptide from the galanin family; and
    administering to the patient an effective amount of ivermectin, metronidazole, clindamycin, azelaic acid, ketoconazole, permethrin, sodium sulfacetamide-sulfur, tretinoin, erythromycin, tetracycline, minocycline, isotretinoin, doxycycline, doxycycline monohydrate, or fusidic acid, wherein the effective amount is effective in eliminating at least one symptom of rosacea.

6. The method according to claim 3, wherein the step of monitoring the expression of the at least one peptide from the galanin family comprises measuring an amount of mRNA coding for the peptide(s).

7. The method according to claim 2, wherein the biological fluid sample is at least one tear.

8. The method according to claim 2, wherein the biological fluid sample is saliva.

9. The method according to claim 3, wherein the biological fluid sample is at least one tear.

10. The method according to claim 2, wherein the control sample is prepared from a biological sample from a healthy patient.

11. The method according to claim 3, wherein the control sample is prepared from a biological sample from a healthy patient, a biological sample from a responder to said treatment, a biological sample from a nonresponder to said treatment, or a biological sample from the patient at a different time.

12. The method according to claim 2, further comprising the step of concluding if the measured expression level is moderate or strong compared to the control sample, wherein an expression level that is between 2 and 5 times greater than the expression level of the control sample is moderate, and an expression level that is at least 5 times greater than the expression level of the control is strong.

\* \* \* \* \*